(12) United States Patent
Sidhu et al.

(10) Patent No.: US 9,205,351 B2
(45) Date of Patent: Dec. 8, 2015

(54) COLLECTION SYSTEM FOR PURIFICATION FLOWSTREAMS

(71) Applicant: Waters Technologies Corporation, Milford, MA (US)

(72) Inventors: Harbaksh Sidhu, Allison Park, PA (US); Ziqiang Wang, Lansdale, PA (US); Steven L. Zulli, Lincoln University, PA (US)

(73) Assignee: Waters Technologies Corporation, Milford, MA (US)

( * ) Notice: Subject to any disclaimer, the term of this patent is extended or adjusted under 35 U.S.C. 154(b) by 203 days.

(21) Appl. No.: 14/085,387

(22) Filed: Nov. 20, 2013

(65) Prior Publication Data

US 2014/0190890 A1    Jul. 10, 2014

Related U.S. Application Data

(62) Division of application No. 13/063,571, filed as application No. PCT/US2009/006059 on Nov. 12, 2009.

(60) Provisional application No. 61/199,026, filed on Nov. 12, 2008.

(51) Int. Cl.
   *B01D 15/10*    (2006.01)
   *G01N 30/82*    (2006.01)
   (Continued)

(52) U.S. Cl.
   CPC .............. *B01D 15/10* (2013.01); *G01N 30/82* (2013.01); *G01N 30/02* (2013.01); *G01N 2030/324* (2013.01)

(58) Field of Classification Search
   CPC . G01N 30/82; G01N 30/02; G01N 2030/324; B01D 15/10; B01D 15/40
   USPC .............. 210/635, 656, 659, 101, 137, 143, 210/198.2, 634; 55/319, 434, 459.1, 468; 95/32, 82, 260, 261, 262, 266, 267; 96/101, 193, 194, 200, 204, 209, 220
   See application file for complete search history.

(56) References Cited

U.S. PATENT DOCUMENTS

| | | |
|---|---|---|
| 1,255,395 A | 2/1918 | Duram |
| 1,416,632 A | 5/1922 | Fothergill |

(Continued)

FOREIGN PATENT DOCUMENTS

| | | |
|---|---|---|
| EP | 0379963 A1 | 8/1990 |
| JP | 2007120972 A | 5/2007 |
| JP | 2008093572 A | 4/2008 |

OTHER PUBLICATIONS

PTO Translation No. 15-102787 of Japan Patent No. 2008093572.*

(Continued)

*Primary Examiner* — Ernest G Therkorn
(74) *Attorney, Agent, or Firm* — McCarter & English, LLP; Deborah M. Vernon

(57) ABSTRACT

A collection system for collecting samples from a flowstream (5) exiting a supercritical fluid chromatography system is provided. The collection system comprises: (i) a first back pressure regulator (10) on the flowstream as it exits the chromatography system, (ii) a gas-liquid separator (30) having a tapered and angled dripper (65), which introduces the flow into the separator at an angle tangential to the separator wall; and (iii) one or more fraction collectors (15), wherein the fraction collector is at a reduced pressure collection point, between 100 bar and atmospheric pressure. A collection system for HPLC is also provided, as well as a process for collection of samples from a flowstream.

9 Claims, 10 Drawing Sheets

(51) Int. Cl.
*G01N 30/02* (2006.01)
*G01N 30/32* (2006.01)

(56) References Cited

U.S. PATENT DOCUMENTS

| | | |
|---|---|---|
| 1,823,301 A | 9/1931 | Walker |
| 2,336,430 A | 12/1943 | Wery |
| 2,884,366 A | 4/1959 | Anderson et al. |
| 3,003,580 A | 10/1961 | Lanning |
| RE30,836 E | 12/1981 | Bunnelle |
| 4,478,720 A | 10/1984 | Perrut |
| 4,681,606 A | 7/1987 | Swan, Jr. et al. |
| 4,724,087 A | 2/1988 | Perrut |
| 5,031,448 A | 7/1991 | Saito |
| 6,413,428 B1 | 7/2002 | Berger et al. |
| 6,632,353 B2 | 10/2003 | Berger et al. |
| 7,678,276 B2 | 3/2010 | Matabe |
| 8,262,760 B2 | 9/2012 | Fogelman et al. |
| 2002/0144949 A1 | 10/2002 | Berger et al. |
| 2005/0178149 A1 | 8/2005 | Ikegami et al. |
| 2006/0108285 A1 | 5/2006 | Bounoshita et al. |
| 2008/0010956 A1 | 1/2008 | Fogelman et al. |
| 2009/0206037 A1 | 8/2009 | Shaimi |
| 2012/0006201 A1 | 1/2012 | Folkvang |

OTHER PUBLICATIONS

Berger, C., et al., "Preparative supercritical fluid chromatography," Journal of Chromatography, 1990, vol. 505, pp. 37-43.

Llua-dong, Yin, et al., "Liquid Entrainment in Slurry Bubble Column Reactor", Journal of East China University of Science and Technology, vol. 31, No. 3, 2004, pp. 273-276.

* cited by examiner

FIG. 3D isometric view

FIG. 3E auxilary view

FIG. 3B side view

FIG. 3A front view

COLLECTION SYSTEM FOR PURIFICATION FLOWSTREAMS

CROSS-REFERENCE TO RELATED APPLICATIONS

This application is a divisional of co-pending U.S. patent application Ser. No. 13/063,571, filed Jun. 17, 2011, which is National Stage filing of International Application No. PCT/US2009/006059, filed Nov. 12, 2009 and designating the United States, which claims the benefit of a priority to U.S. Provisional Patent Application Ser. No. 61/199,026, filed Nov. 12, 2008. The contents of these applications are expressly incorporated herein by reference in its entirety.

FIELD OF THE INVENTION

A continuous collection system for recovery of dissolved solutes from the output stream of a purification system has been developed. The system may be either based on or used with supercritical fluid chromatography (SFC) or extraction (SFE) or other high pressure systems. The collection system may also be used with normal phase or reverse phase chromatography systems such as high performance liquid chromatography (HPLC).

BACKGROUND OF THE INVENTION

In supercritical fluid chromatography, a liquid co-solvent is mixed with a supercritical gas, such as $CO_2$, to vary its strength as a solvent. However, the use of a high pressure system leads to undesired aerosolization of the co-solvent during collection of fractions of the eluting mixed gas liquid solvent stream. This aerosolization causes cross-contamination when attempting to collect separated compounds using a single fraction collection device for depressurization from a continuous stream. Prior art collection systems for supercritical fluid chromatography managed this problem by providing collection systems in which the collection vessels are maintained under high pressure. See, for example, U.S. Pat. Nos. 6,632,353; 6,685,828; 6,413,428; and 6,656,354, each incorporated by reference in its entirety.

It would be desirable to have a collection system which substantially reduces the aerosolization problem by avoiding cross-contamination between fractions from a single continuous stream that are separated by minimal retention time and is operable at atmospheric or near atmospheric pressure. The desired collection system would also eliminate the limitation on number of fractions that can be collected.

SUMMARY OF THE INVENTION

Accordingly, in one aspect the invention provides a collection system for collecting samples from a flowstream exiting a supercritical fluid chromatography system. The collection system comprises:
(i) a first back pressure regulator on the flowstream as it exits the chromatography system;
(ii) a gas-liquid separator having a tapered and angled dripper, which introduces the flow into the separator at an angle tangential to the separator wall; and
(iii) one or more fraction collectors, wherein the fraction collector is at a reduced pressure collection point, between 100 bar and atmospheric pressure.

In another aspect, the invention provides a collection system for collecting samples from a flowstream exiting a high performance liquid chromatography system, the collection system comprising:

i) a solvent make-up pump;
ii) a gas-liquid separator having a tapered and angled dripper, which introduces the flow to the separator at an angle tangential to the separator wall; and
iii) one or more fraction collectors, wherein the fraction collector is at a reduced pressure collection point, between 100 bar and atmospheric pressure.

In an additional aspect, the invention provides a process for collecting samples in a flow stream from a supercritical fluid chromatography system, the flowstream having gas and liquid components, the process comprising the steps of:
ii) reducing the pressure of the flow stream to a pressure between system pressure and atmospheric pressure;
iii) optionally, heating the flow stream;
iv) separating the gas and liquid components in a separator having an angled dripper; and
v) collecting the samples in collection vessels which are at a pressure between atmospheric pressure up to a pressure below system pressure.

These and other aspects of the invention will be more readily apparent from the following drawings, detailed description and appended claims.

DESCRIPTION OF THE DRAWINGS

The invention is further illustrated by the following drawings in which:

FIGS. 3a-3e are diagrams of an embodiment of a dripper of the invention.

FIGS. 4A and 4B are shown on two separate pages. These figures contain same header information.

FIGS. 5A and 5B are shown on two separate pages. These figures contain same header information.

FIGS. 6A and 6B are shown on two separate pages. These figures contain same header information.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

It is to be understood that this invention is not limited to specific compositions, components or process steps disclosed herein, as such may vary. It is also to be understood that the terminology used herein is for the purpose of describing particular embodiments only, and is not intended to be limiting.

Figure 1:
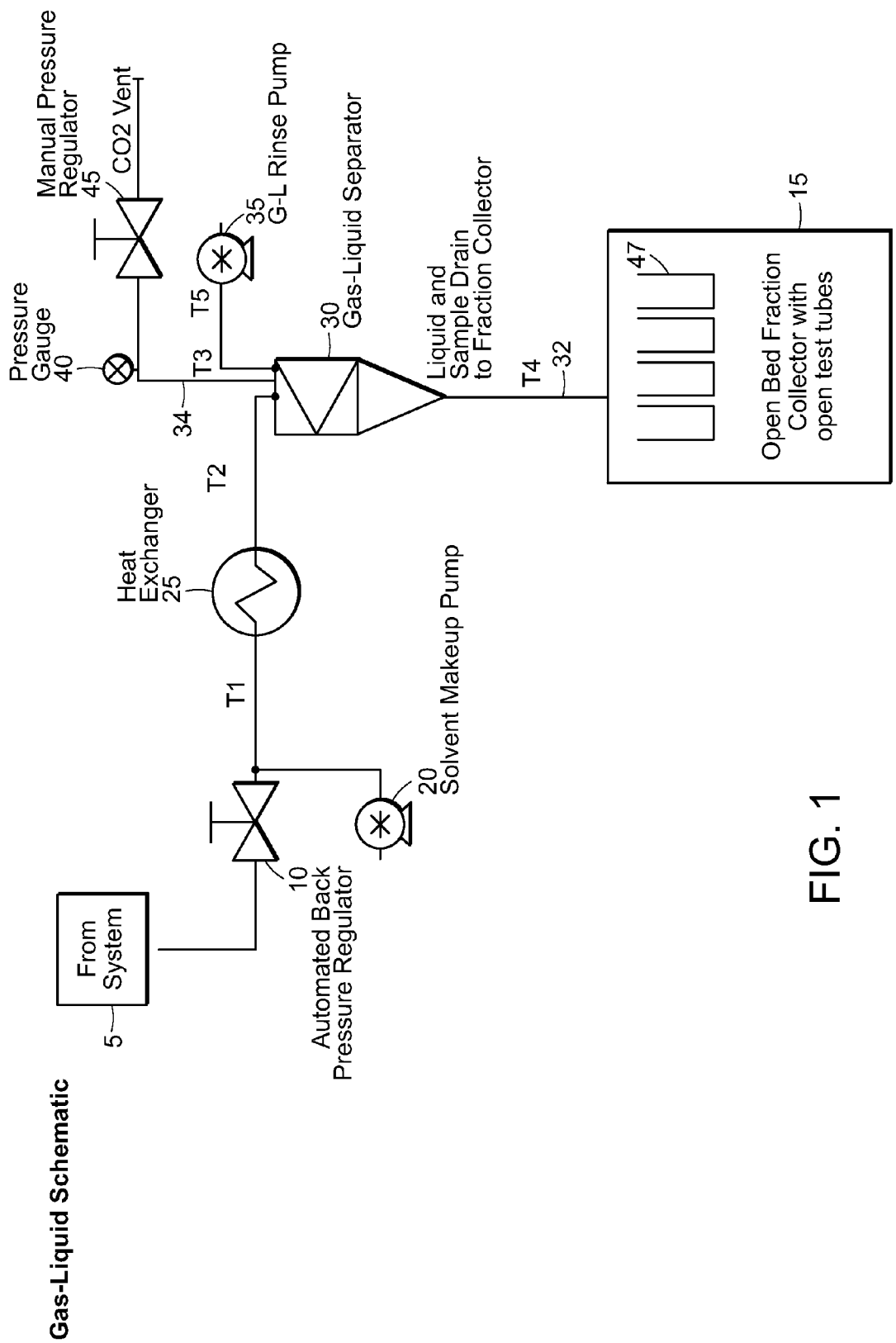
FIG. 1 is a flow diagram of the apparatus in an embodiment of the invention.
Figure 2:
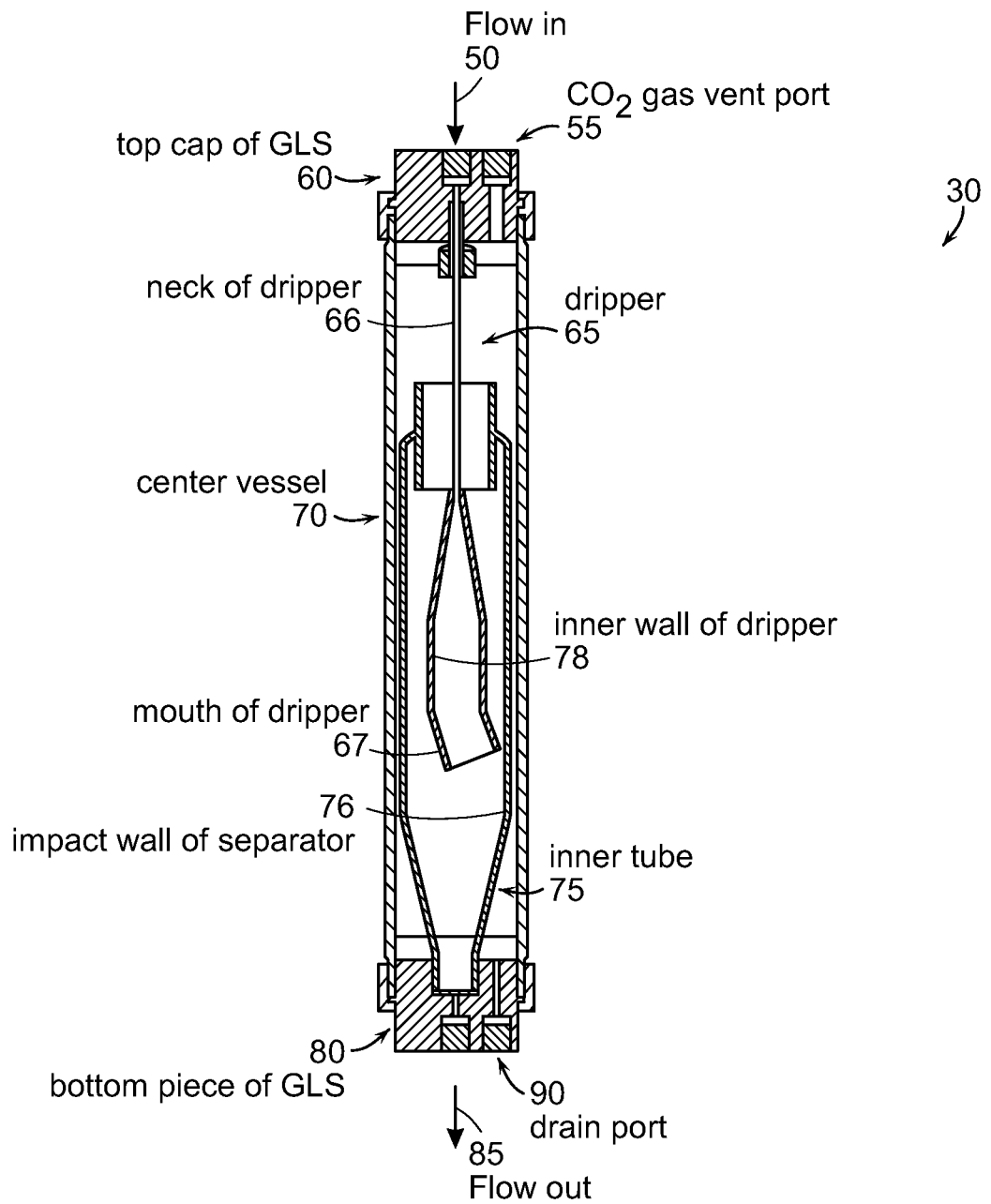
FIG. 2 is a diagram of an embodiment of the gas-liquid separator of the invention.
Figure 3C:
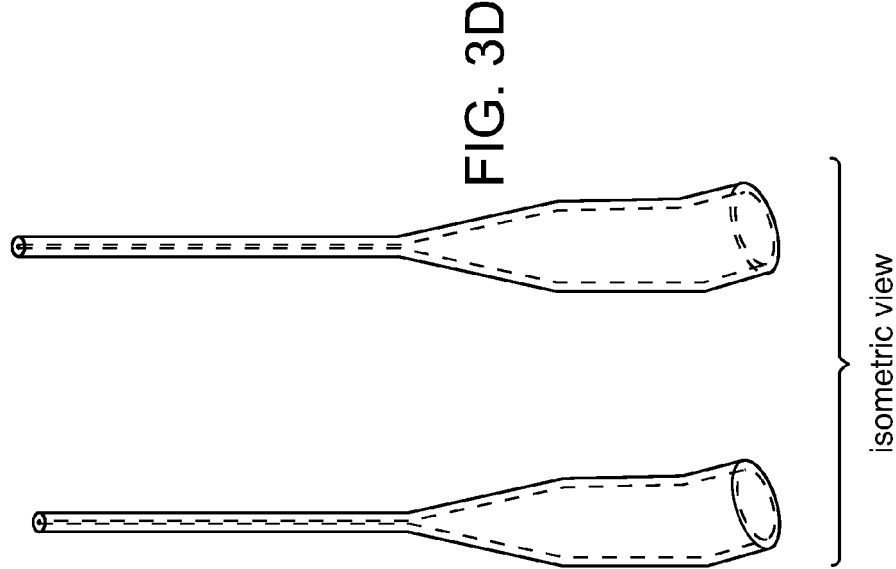
Figure 3C:
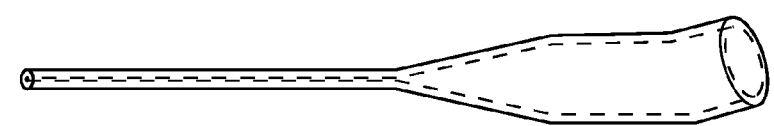
Figure 3C:
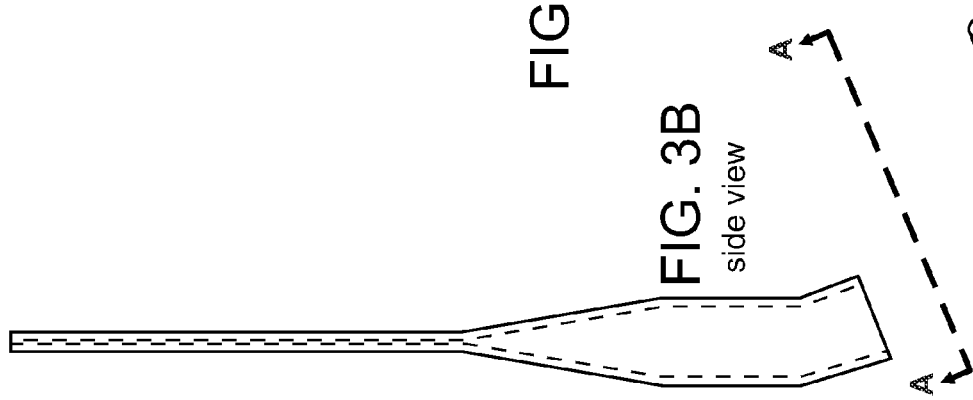
Figure 3C:
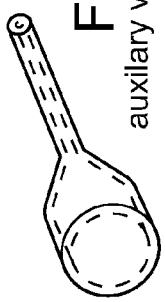
Figure 3C:
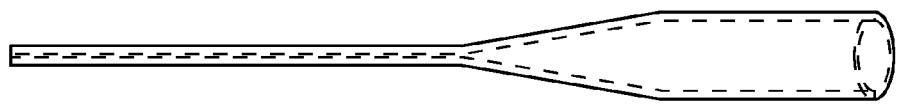
Figure 4A:
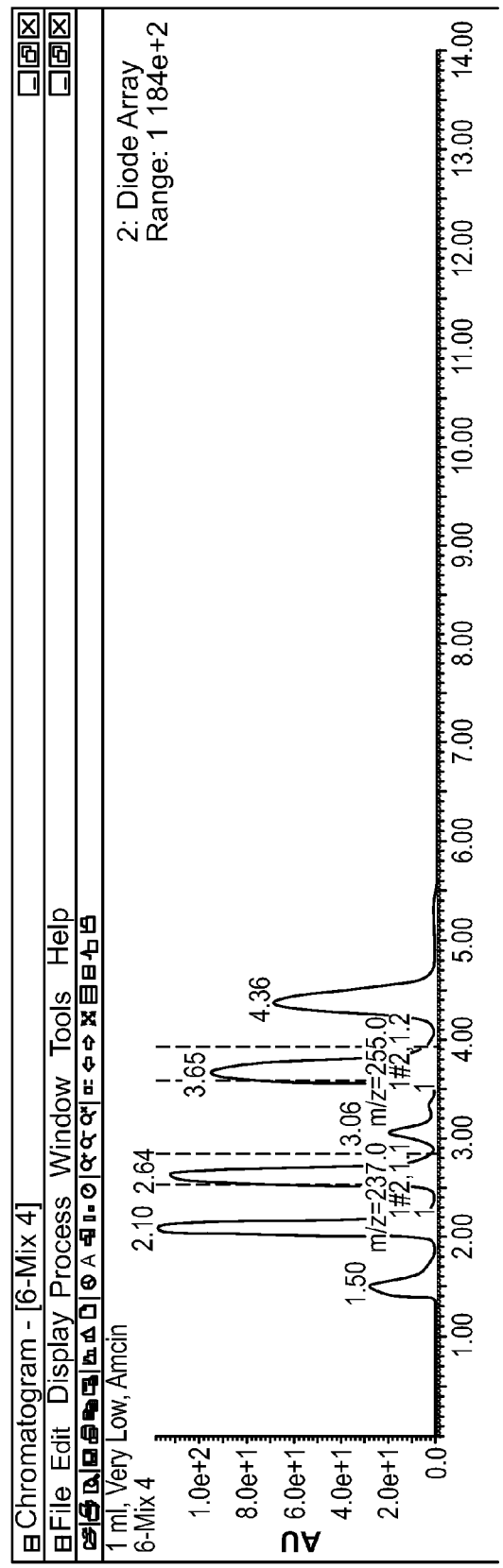
FIGS. 4A and 4B are chromatograms showing fractions (two fractions) being collected from a single stream into a single gas-liquid separator of the invention. For clarity.
Figure 4B:
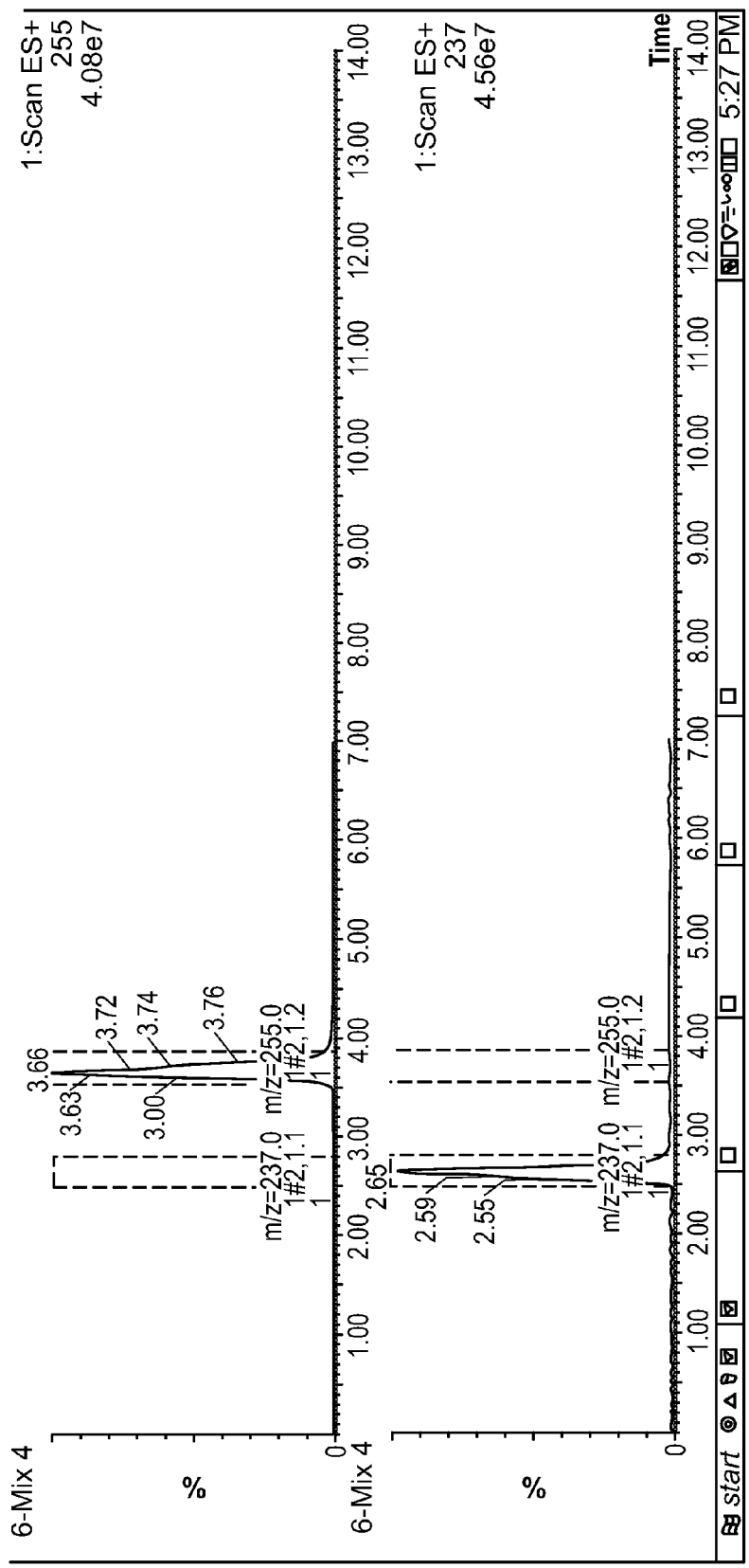
Figure 5A:
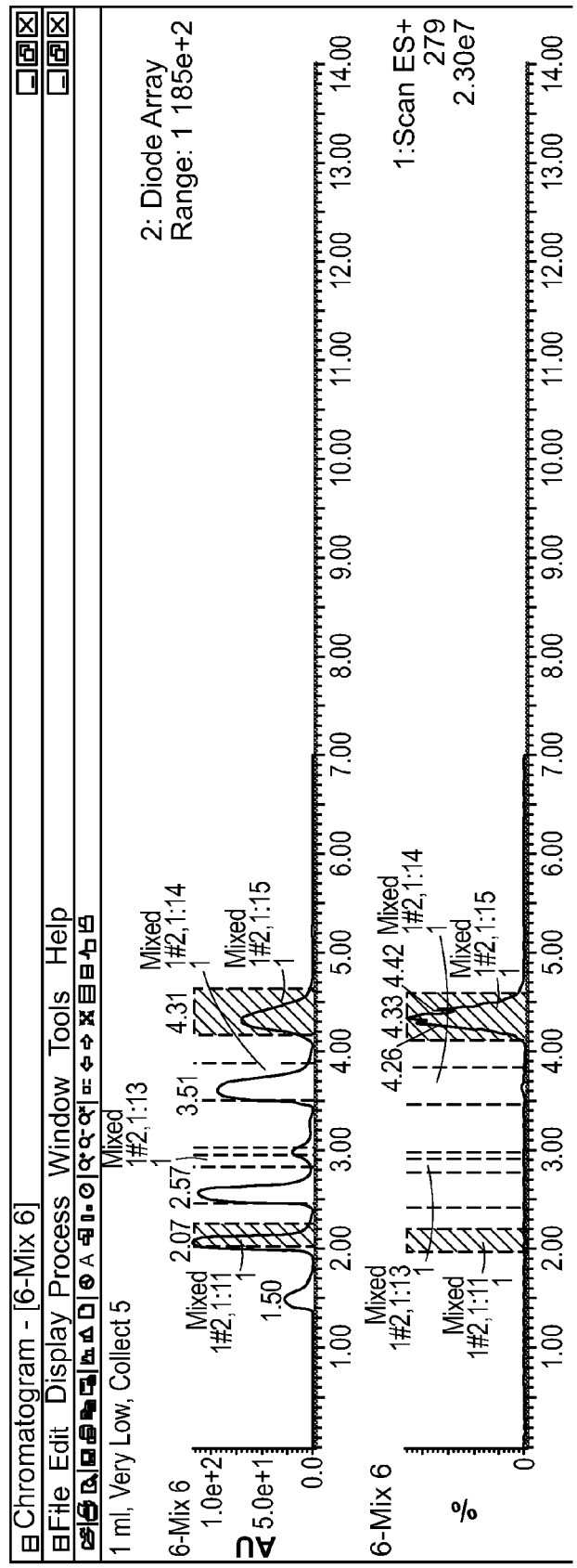
FIGS. 5A and 5B are chromatograms showing fractions (multiple collections in same run) being collected from a single stream into a single gas-liquid separator of the invention. For clarity.
Figure 5B:
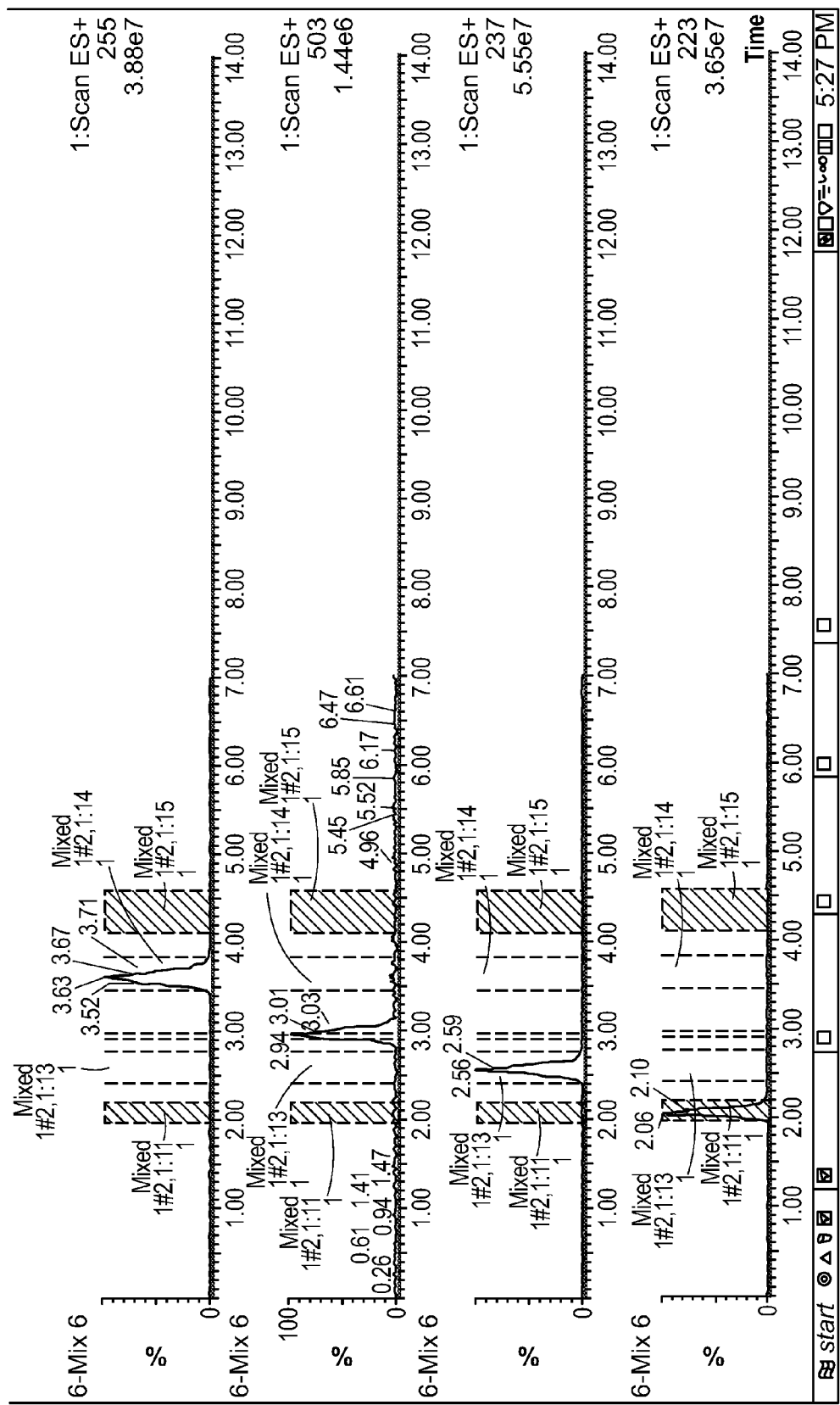
Figure 6A:
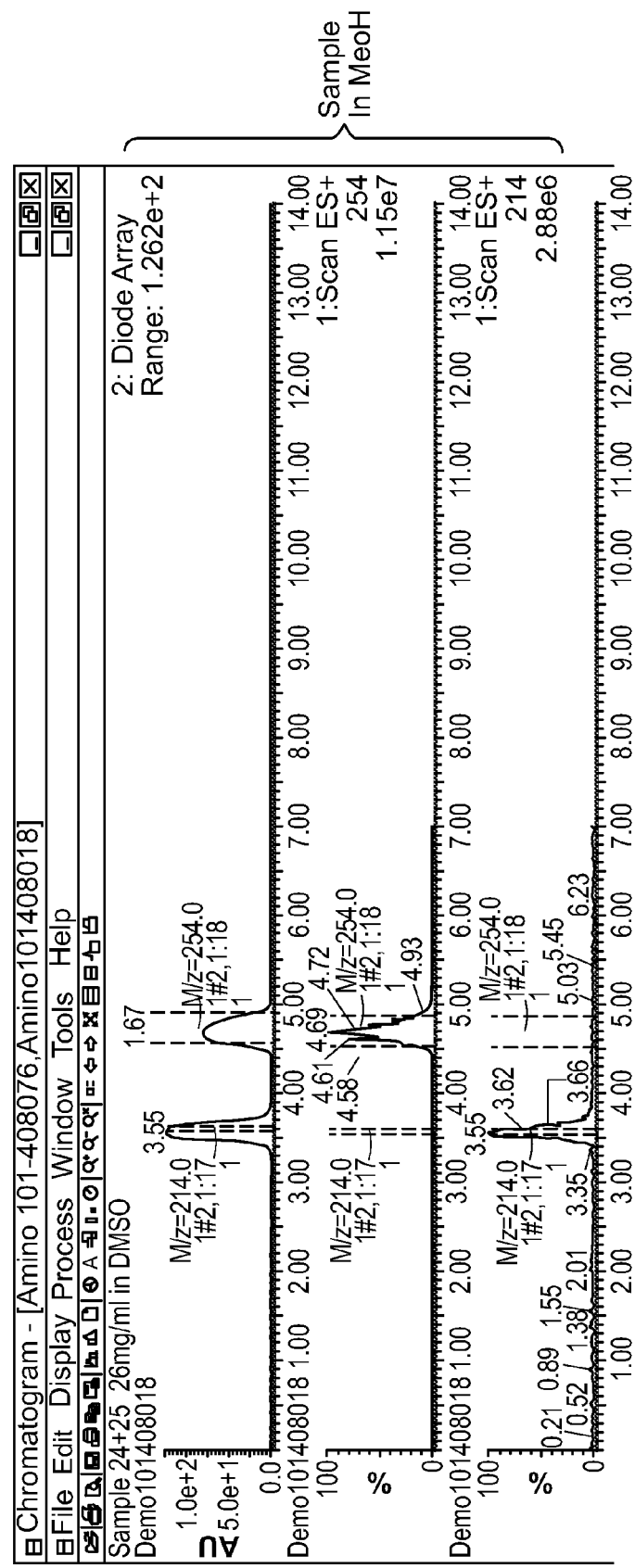
FIGS. 6A and 6B are chromatograms showing fractions being collected from a single stream into a single gas-liquid separator of the invention. For clarity.
Figure 6B:
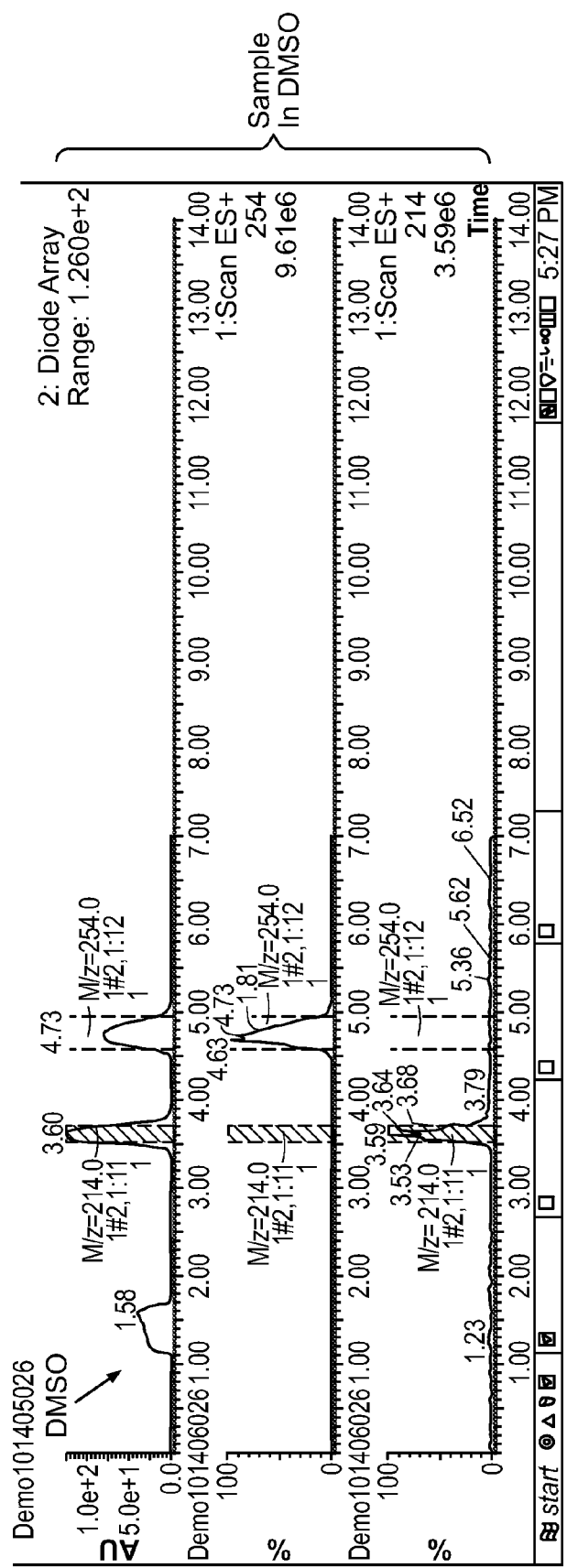
Figure 7:
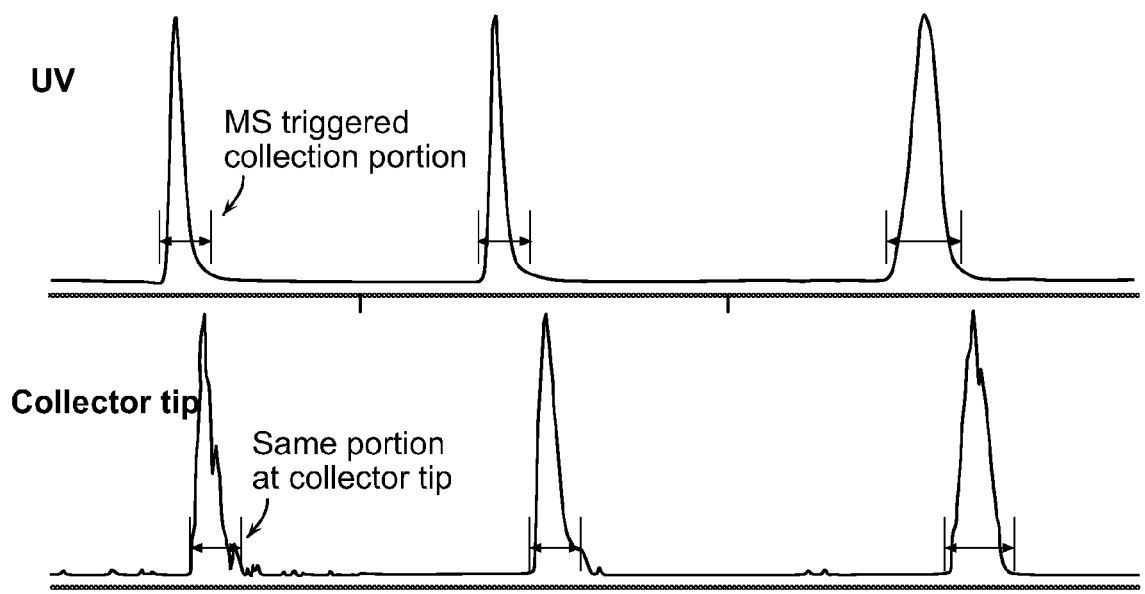
FIG. 7 illustrates the capture of the fraction using the methods and system of the invention.

Referring to FIGS. 1-3, in the system and method of the invention an output flow stream 5 from a chromatography system flows through an automated back pressure regulator 10 toward a fraction collector 15, the fraction collector 15 maintained at a reduced pressure setting (reduced relative to the pressure used in the chromatography or extraction system), preferably at atmospheric pressure. Preferably, the fraction collector is an open bed collector, although collectors that require a pressure above atmospheric pressure, for example up to below system pressure, about 100 bar. As used herein, the term "below system pressure" refers to a pressure of up to 100 bar above atmospheric pressure. The flow stream comprises a high pressure, monophasic fluid of 1) one or more incompressible liquids, in solution with 2) one or more highly dissolved gasses, liquefied gasses or supercritical fluids, and 3) dissolved solutes of interest. Incoming flow is reduced from system operating pressure, which is typically 100 bar or greater, to below system pressure down to atmospheric pressure. A first drop in pressure occurs as the flow stream exits the first backpressure regulator 10, to a level that is less than 100 bar and at or above atmospheric pressure (1 bar or 14 psi). For example, the lower limit on pressure is atmospheric pressure or 5, 10, 15, 20, 25, 30, 35, 40, 45, 50, 55, 60, 65, 70, 75, 80, 85, 90, or 95 bar; the upper limit on pressure is less than 100 bar, 95, 90, 85, 80, 75, 70, 65, 60, 55, 50, 45, 40, 35, 30, 25, 20, 15, 10 or 5 bar.

Optionally, a solvent make-up pump 20 can be used to add solvent as necessary to the flow stream as it exits the back pressure regulator 10. Software is used to monitor the level of solvent in the flow stream and to maintain a minimal level of solvent flow, to allow near complete sample recovery. Maintaining the solvent flow within certain levels, for example, at least 10% of the total flow, usually between about 10% to 50% of the total flow, up to maximum system solvent flow, provides a predictable delay in peak flow through the system, and helps prevent peaks from spreading out and overlapping each other. The makeup solvent can be similar to or the same as the co-solvent used in the separation, or similar to the polarity of the compound that is being collected. This conditioning process also further minimizes the presence of aerosols within the flowstream. The determination of makeup solvent level is within the ability of one skilled in the art of chromatography systems, and is based on the solubility of the solute of interest, flow rate, hardware considerations, and other factors.

As the flow stream exits the first backpressure regulator 10 the gas cools with the drop in pressure, and the flow stream usually requires heating (when supercritical fluids are used) to prevent formation of ice. The flow stream is heated via the heat exchanger 25, which monitors the temperature of the flow stream and heats the flow in a controlled manner, to achieve a flow stream comprised of a gaseous phase and a liquid phase. Typically, the flow stream will be maintained at a temperature of about 25° C. to about 100° C., and the temperature will vary depending on the application. For example, if the solute is not thermally stable, a lower temperature may be needed, whereas a solute having a higher freezing point may require a higher temperature. The gaseous phase is comprised in the majority of the original dissolved or liquefied gaseous or supercritical components as well as a minor portion of evaporated liquid. The liquid phase is comprised primarily of the original liquid components (co-solvent) of the high pressure monophasic stream and dissolved solutes, as well as a minor amount of dissolved gasses from the gaseous phase.

Preferably, the flowstream is introduced into a single cylindrical vapor liquid separator 30 from which the majority of the gaseous and liquid phases exit by separate paths 32, 34. Alternatively, more than one separator, placed in series or in parallel, can be used. However, in contrast to prior art collection systems which use multiple gas-liquid separators to allow separation of the gas and liquid phases, where the liquid exits downward via gravity, and the gas exits upwards via pressure, the collection system of the invention needs only a single gas-liquid separator.

The gas-liquid separator is shown in more detail in FIG. 2. The separator comprises an inlet flow port 50, a gas vent 55, a top cap 60, an outer vessel 70, an inner tube 75, a bottom cap 80, a liquid outflow port 85, and a drain port 90. A specially tapered tube with an increasing internal diameter, called the dripper 65, is inserted into the separator. The mouth of the dripper 67 (through which the flow exits the dripper into the separator, the outlet) is wider than the diameter of the dripper where the flow enters the dripper 66 (inlet). The dimensions of the dripper are optimized for the system's flow rates, which assist in consolidating aerosol into a unified liquid stream. In general, the ratio of the diameter of the outlet to the diameter of the inlet is between 2-100 to 1. For flow rates up to about 100 gm/minute, the ratio of the diameter of the outlet to the diameter of the inlet is between about 2-4 to one, preferably about three to one. The ratio can be adjusted to accommodate flow rates of up to 1000 gm/minute.

Upon entry, the flow stream mixture is directed to impact an inner wall 78 of the dripper at an angle tangential to the impact wall 76 of the separator, is preferably less than 45 degrees. This is the angle of the dripper's outlet in reference to a tangential plane at the impact point on the impact wall. This angle is not necessarily in a vertical orientation, and is the tangential angle. The angle of the dripper, relative to the separator's downward pointing vertical axis is between 10 and 80 degrees. In other words, the exit of the dripper is neither straight down nor straight sideways, but rather in-between. This angle is in a vertical orientation, and is not the tangential angle, and preferably less than 45 degrees. Coalescence starts inside the dripper, and continues at the impact point for the liquid droplets of the stream. The dripper reaches down into the separator more than half way, minimizing the length of liquid flow path in the separator. The impact point and angle of impact serve to direct the liquid stream into a downward spiral toward the liquid exit point 85. The liquid then drains toward the bottom of the separator into the fraction collector 15 and collection vessels 47, such as test tubes, while the gaseous component rises to the gas vent exit 55 near the top of the separator. A second backpressure regulator 45 controls the internal pressure of the separator, controlling the pressure of the gas as it leaves the separator, and providing a force for driving the solvent to the fraction collector.

The volume of the dripper 65 is substantially less than the volume of the inner tube 65 of the separator, approximately 50-100 times less for a flow rate of 100 g/min. The sizes of both the separator and dripper are optimized for the system's flow rate, resulting in a smaller dead volume and lower cross contamination. The internal cavity of the separator is maintained at an elevated pressure, for example, between about 1 bar to 100 bar, by means of the fixed or tunable flow restrictor (the second backpressure regulator 45 through which the gaseous flowstream passes. The internal pressurization provides two important functions. First, it reduces the kinetic energy of the gaseous components entering the separator. This provides less shearing force between vapor and liquid components of the entering stream. The benefits of lower shearing forces on the liquid phase include: 1) lower impact velocity of liquid droplets on the separator wall which results in dramatically lower re-aerosolization of the liquid phase; and 2) lower overall volume requirement for the separator which reduces the steady-state volume of liquid held in the chamber at any given composition of gas and liquid entering the separator. Internal pressurization further provides a driving force to remove the liquid through a second restrictive path originating near the bottom of the container. The restriction of the liquid flow path is selected to allow drainage slightly faster than the highest desired flow rate of liquid into the separator, as determined by the system flow rate. The restriction insures that the majority of entering gas phase components exit through the gas vent flowstream.

The embodiment depicted in FIGS. 2 and 3 is designed for flow rates of up to about 100 gm/minute. As will be appreciated by one skilled in the art, the system can be scaled up or down, depending on the needs of the user. For example, the system can be modified for use with flow rates anywhere between 10 and 1,000 gm/minute. The goal in designing a system that will work with a particular flow rate is to provide the appropriate reduction in velocity of the flow stream as it enters the separator, to minimize aerosolization of the liquid portion of the flow stream. Experimentation to optimize elements in a collection system is routinely conducted by those skilled in the art.

The use of the dripper also eliminates the need for any baffle element near the gas vent since there is little liquid carried upwards along the separator wall. The liquid flowstream exiting the separator can be diverted by a valve to a variety of collection reservoirs. Such collection reservoirs may be intended for either recovery of desirable solutes in the liquid phase, or as a storage point for undesired solutes and solvents from the flow stream.

The collection system can be easily automated in several ways. Selection of a multiport valve or a series of valves can direct multiple discrete flow segments to separate collection vessels. Also, since the flowstream is primarily liquid with a minor amount of entrained gas, it can be adapted to commercially available fraction collection systems, such as those used in HPLC systems, with only minor modifications. Optionally, a rinse solvent can be pumped into the separation chamber through a rinse pump to clean the separator in between sample collection or sample runs.

The system can also be modified and optimized in additional ways. For example, in one embodiment, automation of the separator pressure control can be used to minimize excess gas exiting through the liquid path, by dynamically optimizing pressure for the current flow rate and gas/liquid ratio.

In an additional embodiment, the separator can be heated to a level, determined by the heat exchange capacity of the flows, by means of an infrared or resistive heating element to further drive out dissolved gasses and further minimize residual aerosols.

In further embodiments, automated rinsing of the chamber walls can be implemented, to minimize carryover between individual samples. The system can also be extended to multiple separators for parallel or serial collections, depending on the needs of the user.

In FIGS. 3a-3e three-dimensional drawings of a dripper of the invention is illustrated.

In further embodiments, for a high gas flow rate system, an initial separator could be optimized to separate the majority of the gas phase, diverting the liquid phase and the remaining portion of the gas phase to a second separator. The second separator would be optimized for lower gas flows, and would complete the separation of the gas and liquid phases.

Whereas particular embodiments of this invention have been described above for purposes of illustration, it will be evident to those skilled in the art that numerous variations of the details of the present invention may be made without departing from the invention as defined in the appended claims.

What is claimed is:

1. A process for collecting samples in a flow stream from a supercritical fluid chromatography system, the flowstream having gas and liquid components, the process comprising the steps of:
   i) reducing the pressure of the flow stream to a pressure between system pressure and atmospheric pressure;
   ii) optionally, heating the flow stream;
   iii) separating the gas and liquid components in a separator having a tapered and angled dripper which introduces the flow to the separator at an angle tangential to the separator wall; and
   iv) collecting the samples in collection vessels which are at a pressure between atmospheric pressure up to a pressure below system pressure.

2. The process of claim 1, wherein the separator is maintained at a pressure below system pressure.

3. The process of claim 1, wherein the separator is maintained at a pressure of about 1 bar to about 100 bar.

4. The process of claim 1, wherein the angle of the dripper is between 10 and 80 degrees from vertical.

5. The process of claim 1, wherein the ratio of the volume of the separator to the volume of the dripper is between about 10 and 1000 to one.

6. The process of claim 1, wherein the ratio of the diameter of the dripper outlet to the diameter of the dripper inlet is between 2 and 100.

7. The process of claim 1, wherein the flow rate of the flow stream is between 10 and 1000 gm/minute.

8. The process of claim 1, further comprising the step of heating the flow stream.

9. The process of claim 8, wherein the heated flow stream is maintained at a temperature of about 25° C. to about 100° C.

* * * * *